United States Patent [19]

Chung et al.

[11] Patent Number: 5,192,277
[45] Date of Patent: Mar. 9, 1993

[54] DISPOSABLE ABSORBENT ARTICLE

[75] Inventors: Dae B. Chung; Sung S. Suh; Chun S. Kwak, all of Cheongju, Rep. of Korea

[73] Assignee: LUCKY Ltd., Seoul, Rep. of Korea

[21] Appl. No.: 810,430

[22] Filed: Dec. 18, 1991

[30] Foreign Application Priority Data

Dec. 20, 1990 [KR] Rep. of Korea .................... 90-21162

[51] Int. Cl.$^5$ ............................................. A61F 13/15
[52] U.S. Cl. .................................... 604/360; 604/358
[58] Field of Search ...................... 604/358, 360, 361; 527/300

[56] References Cited

U.S. PATENT DOCUMENTS

| 4,734,748 | 3/1988 | Tsubakimoto et al. | 527/300 |
| 4,842,593 | 6/1989 | Jordan et al. | 604/360 |

FOREIGN PATENT DOCUMENTS

2-154071 6/1990 Japan .................................. 604/360

Primary Examiner—Randall L. Green
Assistant Examiner—R. Clarke
Attorney, Agent, or Firm—James D. Hall

[57] ABSTRACT

Disclosed herein is a disposable absorbent article, e.g., a diaper, comprising a flavonoid and a far-infrared radiating ceramic which has improved bacterial inhibition and deodorizing characteristics.

5 Claims, 1 Drawing Sheet

DISPOSABLE ABSORBENT ARTICLE

BACKGROUND OF THE INVENTION

1. Field of the Invention

The present invention relates to a disposable absorbent article such as a diaper, a sanitary napkin and a panty liner which has improved microbial inhibition and deodorizing ability.

2. Description of the Prior Art

Disposable absorbent articles include a diaper, a sanitary napkin and a panty liner which absorb body exudates.

Hitherto, studies for such disposable absorbent articles have been primarily focused on the absorptive capacity of the article; and, as a result, various absorbent polymers with high absorptive power have been developed.

The focus of recent studies is, however, being shifted to the removal of foul smell and the prevention of skin diseases such as dermatitis, rash and redness caused by wearing a disposable absorbent article for a relatively long time. Urine or other exudates absorbed into the absorbent is converted to ammonia by urease produced by skin-flora, i.e., a group of normal microorganisms on skin; and, in turn, the ammonia causes dermatitis, rash or other forms of skin irritation.

Korean Patent Laid-open Publication Nos. 86-8743 and 86-8744 describe that an article containing an inorganic acid or acid funtional residues controls pH and thus protects skin from rashs. However, such an acid-containing article cannot inhibit urease activity of skin-flora which is the root cause of the problem.

Korean Patent Laid-open Publication No. 90-6454 discloses a disposable absorbent article containing certain far-infrared radiating ceramic. This article has limited effect of removing the foul smell initially occurring from body exudates. However, the far-infrared radiating ceramic fails to inhibit the activity of skin-flora; and, therefore, cannot deodorize the foul smell produced beyond the initial period by the action of microorganisms.

Another method commonly practiced in the industry employs chemical sterilizers to treat a disposable absorbent article. However, such chemical sterilizers tend to cause another level of skin irritation due to its toxic property.

SUMMARY OF THE INVENTION

Therefore, the present invention is directed to provide a disposable absorbent article capable of protecting the user from such skin diseases as dermatitis and rash, etc. and effectively removing the foul smell therefrom.

In accordance with the present invention, it is found that flavonoid compounds have an excellent inhibitory property against the skin-flora, in addition to their well-known deodorizing ability. Further, flavonoid compounds and far-infrared radiating ceramic materials, when combined, have a synergistic effect in enhancing both the inhibitory and the deodorizing activities.

A primary object of the present invention is, therefore, attained by way of providing a disposable absorbent article which incorporates one or more flavonoids and one or more far-infrared radiating ceramics in the matrix materials made of, e.g., a liquid-permeable top sheet, superabsorbent polymer, fluff pulp and a liquid-proof back sheet.

BRIEF DESCRIPTION OF THE DRAWING

The present invention may become more apparent from the detailed description given below with reference to the accompanying drawing, which is given by way of illustration only and thus not limitative of the present invention.

DETAILED DESCRIPTION OF THE INVENTION

Figure 1:
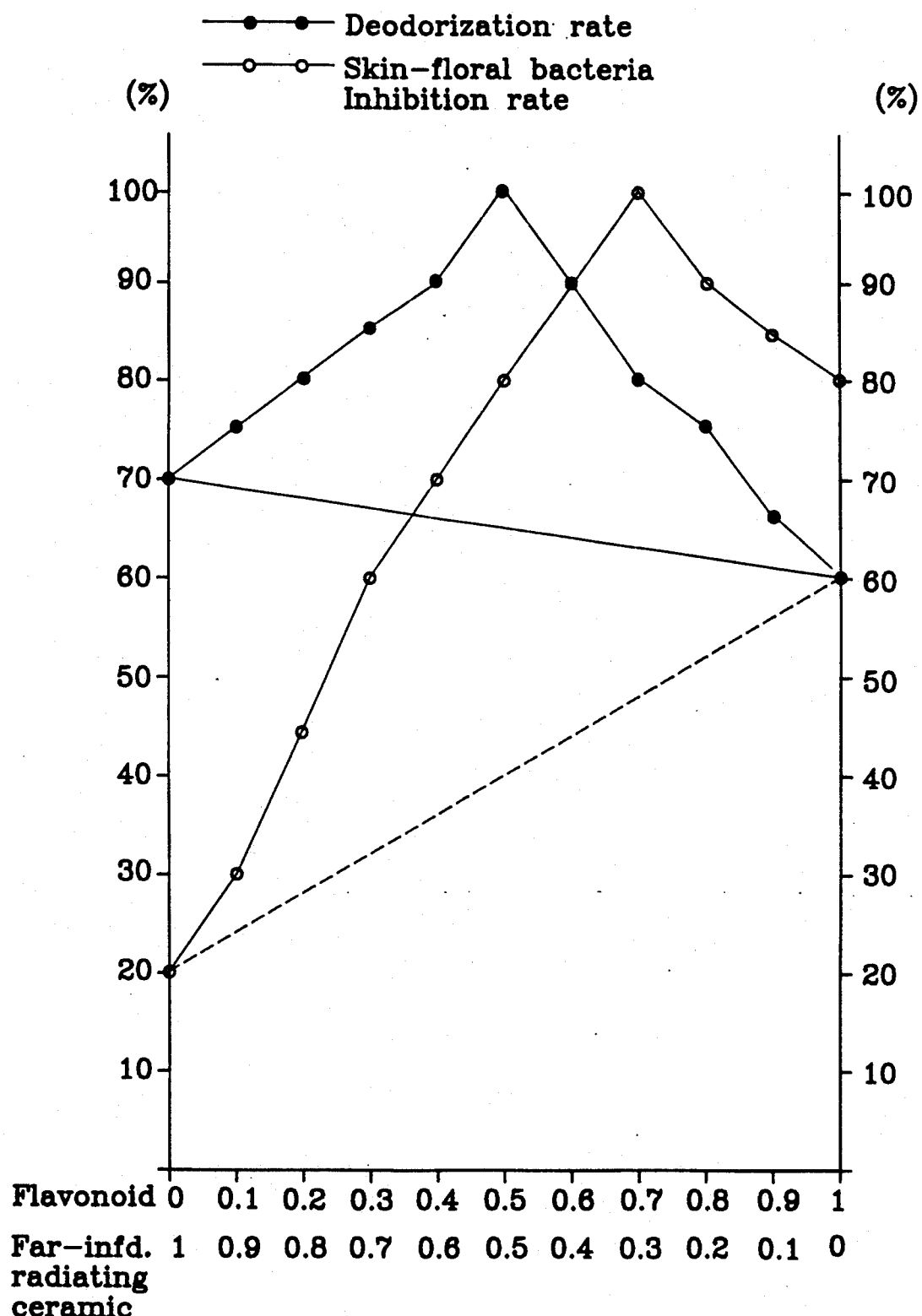
FIG. 1 shows how the mixing ratio of a flavonoid and a far-infrared radiating ceramic interrelates with the inhibitory and the deodorizing activities.

Flavonoids are well-known as a deodorizer; however, they are not hitherto known to have an inhibitory activity against skin-flora or any other microorganisms. The present invention discloses that a disposable absorbent article comprising a flavonoid inhibits the activity of certain microorganisms typically those belonging to genus Candida (i.e., the urease activity of the microorganisms), thereby prevents the synthesis of chemicals, e.g., ammonia, which cause skin diseases and/or foul odor.

Flavonoid compounds useful in the present invention normally contain a flavon skeleton represented by the following formula(I):

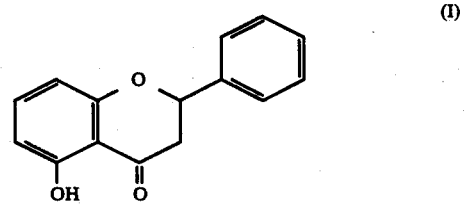

Representative flavonoid compounds include those having the following structural formula(I')

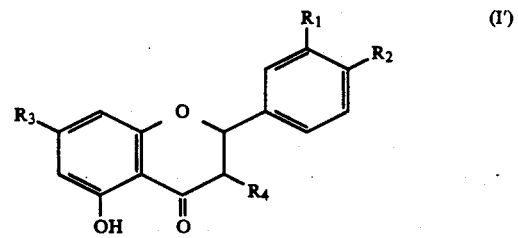

wherein $R_1$, $R_2$, $R_3$ and $R_4$ are as shown in Table 1.

TABLE 1

| Name | $R_1$ | $R_2$ | $R_3$ | $R_4$ |
|---|---|---|---|---|
| Diosmetin | —OH | —OCH₃ | —OH | —H |
| Diosmin | —OH | —OCH₃ | —ORG | —H |
| Eriodictin | —OH | —OH | —OR | —H |
| Eriodictyol | —OH | —OH | —OH | —H |
| Hesperidin | —OH | —OCH₃ | —ORG | —H |
| Hesperetin | —OH | —OCH₃ | —OH | —H |
| Koempferol | —H | —OH | —OH | —OH |
| Naringenin | —H | —OH | —OH | —H |
| Naringin | —H | —OH | —ORG | —H |
| Quercetin | —OH | —OH | —OH | —OH |
| Rutin | —OH | —OH | —ORG | —OH |

*R: Rhamnoside
*RG: Rhamnoglucoside

It is supposed that the inhibitory activity of a flavonoid against skin-flora is achieved by its chemical actions, such as polymerization and addition, with malodorous components as well as physical actions such as absorbence of such components.

Far-infrared radiating ceramics as referred to in this specification mean those materials radiating far-infrared rays having the wave length ranging from 6 to 14 μm, preferably 7.6 to 12 μm. Such a ceramic comprises various components such as those shown in Table 2, given as an illustrative composition only.

TABLE 2

| Component | Content (%) | Component | Content (%) |
|---|---|---|---|
| $SiO_2$ | 68.13 | CaO | 1.50 |
| $Al_2O_3$ | 18.70 | $Fe_2O_3$ | 0.07 |
| $Na_2O_3$ | 6.80 | The other | 0.20 |
| $K_2O$ | 4.60 | | |

Far-infrared radiating ceramics are known to have a deodorizing activity and a limited inhibitory activity against skin-flora. However, it is found in accordance with the present invention that said far-infrared radiating ceramics exhibit a synergistic effect when combined with a flavonoid with respect to the above two activities. That is, a disposable absorbent article containing a flavonoid and a far-infrared radiating ceramic exhibits a surprisingly stronger activity of deodorization and superior microbial inhibition than an article containing either one of the above two components.

The synergistic effect may be observed almost at any composition ratio of flavonoid and far-infrared ceramic. However, the article containing the two shows a more pronounced synergistic effect when the flavonoid compound and the far-infrared radiating ceramic is provided in a ratio ranging from 2:8 to 8:2 by weight, and, more preferably, 4:6 to 8:2.

The mixture of a flavonoid and a far-infrared radiating ceramic may be incorporated into the disposable absorbent article in various ways: e.g., by way of introducing it directly to the liquid-permeable top sheet; the superabsorbent polymer; the fluff pulp; the barrier cuff; the tissue; or the entire layers or constituents of the disposable absorbent article during the preparation thereof.

The mixture of a flavonoid and a ceramic may be preferably employed in a range from 0.1 to 20% by weight of the whole disposable absorbent article.

When the amount is less than the above lower limit, the deodorizing activity is weak; and when the amount is more than the upper limit the content of fluff pulp and superabsorbent polymer is relatively decreased and thus the absorptive capacity becomes compromised.

The present invention will be further illustrated by way of the following examples.

EXAMPLES 1-9 AND COMPARATIVE EXAMPLES 1,2

Disposable diapers were prepared by a conventional method; except that a mixture of a flavonoid(FRESH SHIRAIMATSU FS-1000, Shiraimatsu Shinyaku Co., Ltd., Japan) and a far-infrared radiating ceramic(in powder, OK Trading, Japan) was added to each of the diapers in the weight ratio of 0.10[Comparative Example 1], 1:9 [Example 1], 2:8[Example 2], 3:7[Example 3], 4:6[Example 4], 5:5 [Example 5], 6:4[Example 6], 7:3[Example 7], 8:2[Example 8], 9:1 [Example 9] and 10.0[Comparative Example 2 ], respectively. The total amount of the flavonoid and the far-infrared radiating ceramic was always kept at 1 wt.% for each disposable diaper. The mixture was added, in order to prepare three diaper samples for each Example, by way of:

(1) spreading the mixture over the tissue;
(2) spreading it over the fluff pulp; and
(3) mixing it with the fluff pulp.

CONTROL

Control disposable diapers were prepared by the same method as in Examples 1-9, except that neither the flavonoid nor the far-infrared radiating ceramic was added.

COMPARATIVE EXAMPLE 3

Disposable diapers were prepared by the same method as in Examples 1-9; except that a chemical sterilizer, Katon CG(Rohm and Hass Company), was added instead of the flavonoid/ceramic mixture.

The disposable diapers prepared in Examples 1-9 and Comparative Examples 1 and 2 were tested to measure their deodorization and skin-flora inhibition effect.

DEODORIZATION EFFECT TEST

Each disposable diaper was applied with 5 g of baby's feces and placed into a sealed 5 l chamber kept at a temperature of 38° C. After 5 minutes, the initial ammonia concentration was measured by using the gastic reactotube method employing Kitagawa AP-1 gas detector(Komyo, Japan) and 3M, 3L, 3La of gastic reactotubes(Gastec, Japan). After 1 hour, the ammonia concentration was measured again by the same method as above.

The above test was repeated 3 times for each of the Examples and Comparative Examples, and the average of the three measured values was recorded as the ammonia concentration value.

The deodorization rate was calculated from the ammonia concentration values in accordance with the following equation:

$$\text{Deodorization Rate}(\%) = \left(1 - \frac{\text{ammonia concentration value after 5 minutes}}{\text{ammonia concentration value after 1 hour}}\right) \times 100$$

The results are shown in Table 3 and FIG. 1.

TABLE 3

| | Content of Katon CG (wt. %) | Content of flavonoid (wt. %) | Content of far-infrared radiating ceramic (wt. %) | Ammonia concentration (ppm) After 5 min. | Ammonia concentration (ppm) After 1 hour | Deodorization rate (%) |
|---|---|---|---|---|---|---|
| Control | 0 | 0 | 0 | $2.0 \times 10^2$ | $2.0 \times 10^2$ | 0 |
| Comparative Example 1 | 0 | 0 | 1 | $2.0 \times 10^2$ | $0.8 \times 10^2$ | 60 |
| Example 1 | 0 | 0.1 | 0.9 | $2.0 \times 10^2$ | $0.5 \times 10^2$ | 75 |
| Example 2 | 0 | 0.2 | 0.8 | $2.0 \times 10^2$ | $0.4 \times 10^2$ | 80 |
| Example 3 | 0 | 0.3 | 0.7 | $2.0 \times 10^2$ | $0.3 \times 10^2$ | 85 |
| Example 4 | 0 | 0.4 | 0.6 | $2.0 \times 10^2$ | $0.2 \times 10^2$ | 90 |
| Example 5 | 0 | 0.5 | 0.5 | $2.0 \times 10^2$ | 0 | 100 |

TABLE 3-continued

| | Content of Katon CG (wt. %) | Content of flavonoid (wt. %) | Content of far-infrared radiating ceramic (wt. %) | Ammonia concentration (ppm) | | Deodorization rate (%) |
|---|---|---|---|---|---|---|
| | | | | After 5 min. | After 1 hour | |
| Example 6 | 0 | 0.6 | 0.4 | $2.0 \times 10^2$ | $0.2 \times 10^2$ | 90 |
| Example 7 | 0 | 0.7 | 0.3 | $2.0 \times 10^2$ | $0.4 \times 10^2$ | 80 |
| Example 8 | 0 | 0.8 | 0.2 | $2.0 \times 10^2$ | $0.55 \times 10^2$ | 73 |
| Example 9 | 0 | 0.9 | 0.1 | $2.0 \times 10^2$ | $0.7 \times 10^2$ | 65 |
| Comparative Example 2 | 0 | 1 | 0 | $2.0 \times 10^2$ | $0.6 \times 10^2$ | 70 |
| Comparative Example 3 | 1 | 0 | 0 | $2.0 \times 10^2$ | $2.0 \times 10^2$ | 0 |

SKIN-FLORA INHIBITION TEST

Each disposable diaper was applied with 100 g of baby's urine and inoculated with about $10^6$ microorganisms of *Candida albicans*, one of the common skin-floral microorganisms, per 1 g of urine. Said each disposable diaper was placed into a sealed 5 l chamber and incubated at 38° C. After 1 hour, the ammonia concentration was measured by the gastic reactotube method using Kitagawa AP-1 gas detector(Komyo, Japan) and 3M, 3L and 3La gas reactotubes(Gastec, Japan).

The above test was repeated 3 times for each of Examples and Comparative Examples; and the average of the three measured values was recorded as the ammonia concentration value.

Inhibition rate against the microorganisms was calculated from the ammonia concentration values in accordance with the following equation:

Inhibition rate against microorganisms (%) =

$$\left(1 - \frac{\text{Ammonia conc. value in Ex. or Comp. Ex.}}{\text{Ammonia conc. value in Control}}\right) \times 100$$

The results are shown in Table 4 and FIG. 1.

DERMATITIS AND RASH PREVENTION TEST

Each disposable diaper was put on by 100 babies of 3 to 12 month old for 4 days, changing the diaper about 8 times per day; and then the number of babies having diaper rash was counted. The results are shown in Table 4.

As shown in Tables 3 and 4, the disposable diapers prepared in Examples are possessed with a superior deodorization and microbial inhibition effect to those prepared in Comparative Examples; and, as clearly shown in FIG. 1, the disposable diapers containing both a flavonoid and a far-infrared radiating ceramic, in accordance with the present invention, are capable of producing the deodorization and microbial inhibition effects much stronger than the expected theoretical values, i.e., sums of the respective effects measured from the disposable diapers containing either a flavonoid or a ceramic alone.

What is claimed is:

1. In an improved disposable absorbent article comprising a liquid-permeable top sheet, a superabsorbent polymer core, a fluff pulp layer and a liquid-proof back sheet, the improvement which comprises a mixture of a flavonoid and a far-infrared radiating ceramic incorporated in the top sheet, the polymer core, the fluff pulp layer and/or the back sheet.

2. The article of claim 1, wherein the flavonoid and the far-infrared radiating ceramic are used in a ratio ranging from 2:8 to 8:2 by weight.

3. The article of claim 2, wherein said ratio ranges from 4:6 to 8:2.

4. The article of claim 3, wherein the total content of the flavonoid and the far-infrared radiating ceramic is in a range from 0.1 to 20% of the article by weight.

5. The article of claim 1, wherein the flavonoid is a flavon derivative selected from the group consisting of diosmetin, diosmin, eriodictin, eriodictyol, hesperidin, hesperetin, koempferol, naringenin, naringin, quercetin, rutin and a mixture thereof.

* * * * *

TABLE 4

| | Content of flavonoid (wt. %) | Content of far-infd. radiating ceramic (wt. %) | Content of Katon CG (wt. %) | Amount of inoculated *Candida albicans* (of organisms/urine g) | Ammonia concentration (ppm) | Inhibition rate against skin-floral bacteria (%) | No. of babies having diaper rash |
|---|---|---|---|---|---|---|---|
| Control | 0 | 0 | 0 | 0 | 0* | — | — |
| | | | | $10^6$ | $1.0 \times 10^2$ | 0 | 30 |
| Comp. Ex. 1 | 0 | 1 | 0 | $10^6$ | $0.8 \times 10^2$ | 20 | 4 |
| Ex. 1 | 0.1 | 0.9 | 0 | $10^6$ | $0.7 \times 10^2$ | 30 | 2 |
| Ex. 2 | 0.2 | 0.8 | 0 | $10^6$ | $0.55 \times 10^2$ | 45 | 1 |
| Ex. 3 | 0.3 | 0.7 | 0 | $10^6$ | $0.4 \times 10^2$ | 60 | 1 |
| Ex. 4 | 0.4 | 0.6 | 0 | $10^6$ | $0.3 \times 10^2$ | 70 | 0 |
| Ex. 5 | 0.5 | 0.5 | 0 | $10^6$ | $0.2 \times 10^2$ | 80 | 0 |
| Ex. 6 | 0.6 | 0.4 | 0 | $10^6$ | $0.1 \times 10^2$ | 90 | 0 |
| Ex. 7 | 0.7 | 0.3 | 0 | $10^6$ | 0 | 100 | 0 |
| Ex. 8 | 0.8 | 0.2 | 0 | $10^6$ | $0.1 \times 10^2$ | 90 | 0 |
| Ex. 9 | 0.9 | 0.1 | 0 | $10^6$ | $0.2 \times 10^2$ | 80 | 1 |
| Comp. Ex. 2 | 1 | 0 | 0 | $10^6$ | $0.25 \times 10^2$ | 75 | 2 |
| Comp. Ex. 3 | 0 | 0 | 1 | $10^6$ | $0.35 \times 10^2$ | 65 | 43 |

*Note: No traceable amount of ammonia in the control diaper not inoculated with *Candida albicans*